US010113965B2

(12) United States Patent
Simpson et al.

(10) Patent No.: US 10,113,965 B2
(45) Date of Patent: Oct. 30, 2018

(54) METHODS FOR SECOND HARMONIC GENERATION IMAGING OF PROTEIN CRYSTALS

(71) Applicant: PURDUE RESEARCH FOUNDATION, West Lafayette, IN (US)

(72) Inventors: Garth Jason Simpson, West Lafayette, IN (US); Justin Allen Newman, West Lafayette, IN (US); Nicholas Roman Pogranichniy, West Lafayette, IN (US); Nicole Mulready Scarborough, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/555,588

(22) PCT Filed: Mar. 4, 2016

(86) PCT No.: PCT/US2016/020951
§ 371 (c)(1),
(2) Date: Sep. 5, 2017

(87) PCT Pub. No.: WO2016/144781
PCT Pub. Date: Sep. 15, 2016

(65) Prior Publication Data
US 2018/0052103 A1 Feb. 22, 2018

Related U.S. Application Data

(60) Provisional application No. 62/129,497, filed on Mar. 6, 2015.

(51) Int. Cl.
*G02F 1/37* (2006.01)
*G01N 21/63* (2006.01)
(Continued)

(52) U.S. Cl.
CPC ......... *G01N 21/636* (2013.01); *G01N 23/207* (2013.01); *G01N 33/52* (2013.01);
(Continued)

(58) Field of Classification Search
None
See application file for complete search history.

(56) References Cited

U.S. PATENT DOCUMENTS 8,030,077 B2 * 10/2011 Simpson .............. G01N 21/636 356/30
9,778,177 B2 * 10/2017 Roke ...................... G01N 21/47
(Continued)

OTHER PUBLICATIONS

Salafsky, J. S. "'SHG-labels' for detection of molecules by second harmonic generation." Chemical physics letters 342.5-6 (2001): 485-491 (Year: 2001).*
(Continued)

*Primary Examiner* — Shawn Decenzo
(74) *Attorney, Agent, or Firm* — Hartman Global IP Law; Gary M. Hartman; Domenica N. S. Hartman

(57) ABSTRACT

Methods for determining the 3-D structures of proteins. Such a method includes incorporating a compound into a protein crystal such that the compound enhances the activity of the protein crystal to second harmonic generation, illuminating the protein crystal with a sufficiently intense light to cause second harmonic generation by the protein crystal, and detecting a second harmonic generation response produced by the protein crystal that is suitable for protein structure determination by diffraction analysis.

12 Claims, 4 Drawing Sheets

(51) Int. Cl.
*G01N 33/52* (2006.01)
*G01N 33/58* (2006.01)
*G01N 33/68* (2006.01)
*G01N 23/207* (2018.01)

(52) U.S. Cl.
CPC ............. *G01N 33/58* (2013.01); *G01N 33/68* (2013.01); *G02F 1/37* (2013.01)

(56) References Cited

U.S. PATENT DOCUMENTS

| | | | | |
|---|---|---|---|---|
| 2002/0094520 | A1* | 7/2002 | Salafsky | G01N 33/5005 435/5 |
| 2010/0031748 | A1* | 2/2010 | Simpson | G01N 21/21 73/579 |
| 2010/0233820 | A1* | 9/2010 | Pantazis | C12Q 1/6818 436/94 |
| 2012/0241647 | A1* | 9/2012 | Simpson | G01N 21/6402 250/459.1 |
| 2013/0057848 | A1* | 3/2013 | Simpson | G01N 21/636 356/30 |
| 2015/0233820 | A1* | 8/2015 | Roke | G01N 21/47 356/338 |
| 2016/0292354 | A1* | 10/2016 | Salafsky | G01N 33/542 |
| 2017/0268966 | A1* | 9/2017 | Fraden | B01D 9/0072 |

OTHER PUBLICATIONS

Campagnola, Paul. "Second harmonic generation imaging microscopy: applications to diseases diagnostics." (2011): 3224-3231 (Year: 2011).*
Chen, Xiyi, et al. "Second harmonic generation microscopy for quantitative analysis of collagen fibrillar structure." Nature protocols 7.4 (2012): 654 (Year: 2012).*
Haupert, Levi M., Emma L. DeWalt, and Garth J. Simpson. "Modeling the SHG activities of diverse protein crystals." Acta Crystallographica Section D: Biological Crystallography 68.11 (2012): 1513-1521 (Year: 2012).*
Macias-Romero, Carlos, et al. "High throughput second harmonic imaging for label-free biological applications." Optics Express 22.25 (2014): 31102-31112 (Year: 2014).*
Wampler, Ronald D., et al. "Selective detection of protein crystals by second harmonic microscopy." Journal of the American Chemical Society 130.43 (2008): 14076-14077 (Year: 2008).*
International Search Report dated Jun. 27, 2016 for PCT/US16/20951.

* cited by examiner

METHODS FOR SECOND HARMONIC GENERATION IMAGING OF PROTEIN CRYSTALS

CROSS-REFERENCE TO RELATED APPLICATIONS

This application claims priority to co-pending U.S. patent application Ser. No. PCT/US16/20951, filed Mar. 4, 2016, and U.S. Provisional Application Ser. No. 62/129,497, filed Mar. 6, 2015, the contents of which are incorporated herein by reference.

BACKGROUND OF THE INVENTION

The present invention generally relates to three-dimensional (3-D) structural data of protein molecules, and to methods for their determination.

Proteins differ from one another in their sequence of amino acids, which typically results in folding of the protein molecule into a unique 3-D structure referred to as its tertiary structure. The overall shape of this 3-D structure controls the basic function of the protein, and therefore the discovery of its tertiary structure, or the quaternary structure of its complexes, can provide important clues about how the protein functions. X-ray crystallography is one of the major methods used to determine protein structures, but requires that the protein be capable of crystallization in preparation for diffraction analysis. Solved structures are usually deposited in the protein data bank (PDB).

Due to the growing number of new protein targets for crystallization and entry of their protein crystal structures into the PDB, the need for high-throughput technologies for protein crystal analysis has emerged. Currently, numerous imaging modalities are employed for scoring protein crystal "hits" during the crystallization condition screening process. Several instances of fluorescence imaging techniques such as two-photon excited UV fluorescence (TPE-UVF), UV laser-stimulated fluorescence (UVF), covalent modification of the protein with a fluorophore, and noncovalent fluorescent molecule intercalation have appeared in the literature. TPE-UVF utilizes intrinsic fluorescent properties of aromatic residues, e.g., tryptophan, found in most proteins to provide contrast. However, this technique is limited to proteins with high intrinsic fluorescence. For proteins that do not exhibit strong intrinsic fluorescence (due to a lack of tryptophan), such as insulin, UVF has been used for imaging. However, exposing protein crystals to a UV-C band excitation laser has been shown to damage disulfide bonds within the protein. By covalently modifying proteins with fluorophores, researchers have been able to circumvent the need for intrinsic fluorescence and damaging laser wavelengths to visualize proteins. However, this method adds a further sample handling step, and studies have shown that covalent modification can adversely influence the folding structure of the protein. All of the above mentioned techniques suffer from a major limitation due to a lack of selectivity for crystalline protein, producing nonzero signals from crystalline proteins, amorphous protein aggregates, and proteins in solution.

Second harmonic generation (SHG) microscopy has been shown to be a complementary technique for selective imaging of protein crystals. SHG, or the frequency doubling of light, can arise when noncentrosymmetric crystalline material is illuminated by sufficiently intense light, with negligible contributions from disordered media such as protein aggregate. Recently, SHG microscopy has been successfully developed for automated analysis of 96-well plates, assessing crystal quality through polarization analysis, and rapid centering of crystals on a synchrotron beamline. However, current SHG microscopy techniques can only detect an estimated 84% of known protein crystal structures with crystals exhibiting SHG activities spanning several orders of magnitude. For smaller crystals or for high-throughput screening applications with shorter signal integration times, this coverage value will be correspondingly reduced, suggesting the need for improvements in the signal to noise ratio (SNR, or S/N) for crystal detection. The SHG response varies considerably depending upon the protein, the protein orientation within the lattice, and the symmetry of the lattice. The latter of which is the main driving force behind the inability to detect roughly 16% of the current PDB entries. A detailed discussion of the relationships between symmetry, structure, and SHG activity of proteins can be found in Haupert et al., *Acta Crystallographica Section D* 68, p. 1513-1521 (2012), whose contents are incorporated herein by reference.

In view of the above, improving the detection limits of SHG would be desirable to increase the coverage of protein crystals amenable to SHG detection, reduce the time frame required for protein crystal imaging by SHG, and allow detection of increasingly smaller crystals at early stages of crystallization.

BRIEF DESCRIPTION OF THE INVENTION

The present invention provides methods for determining the 3-D structures of proteins.

According to one aspect of the invention, the method includes incorporating a compound into a protein crystal such that the compound enhances the activity of the protein crystal to second harmonic generation, illuminating the protein crystal with a sufficiently intense light to cause second harmonic generation by the protein crystal, and then detecting a second harmonic generation response produced by the protein crystal that is suitable for protein structure determination by diffraction analysis.

Technical effects of methods as described above preferably include the ability to extend the detection range when using SHG microscopy to determine 3-D structures of proteins. Such methods retain advantages of SHG microscopy, including second harmonic generation signals arising from noncentrosymmetric, well-ordered, crystalline material with no coherent signal contribution from amorphous protein, solublized protein, or solublized compound. In addition, by intercalating a suitable compound into a protein molecule after crystallization, the method does not influence the folding structures of the protein. In some cases, the intercalation of certain compounds into formed protein crystals have allowed for second harmonic generation signal enhancements from protein crystals of roughly 1000 fold.

Other aspects and advantages of this invention will be further appreciated from the following detailed description.

BRIEF DESCRIPTION OF THE DRAWINGS

FIGS. 6 and 7 summarize results of screens for malachite green and crystal violet, wherein FIG. 6 represents crystal screen hits from Proteinase K under normal conditions, and FIG. 7 represents crystal screen hits from Proteinase K with the addition of either 50 μM malachite green or 50 μM crystal violet.

DETAILED DESCRIPTION OF THE INVENTION

Figure 1:
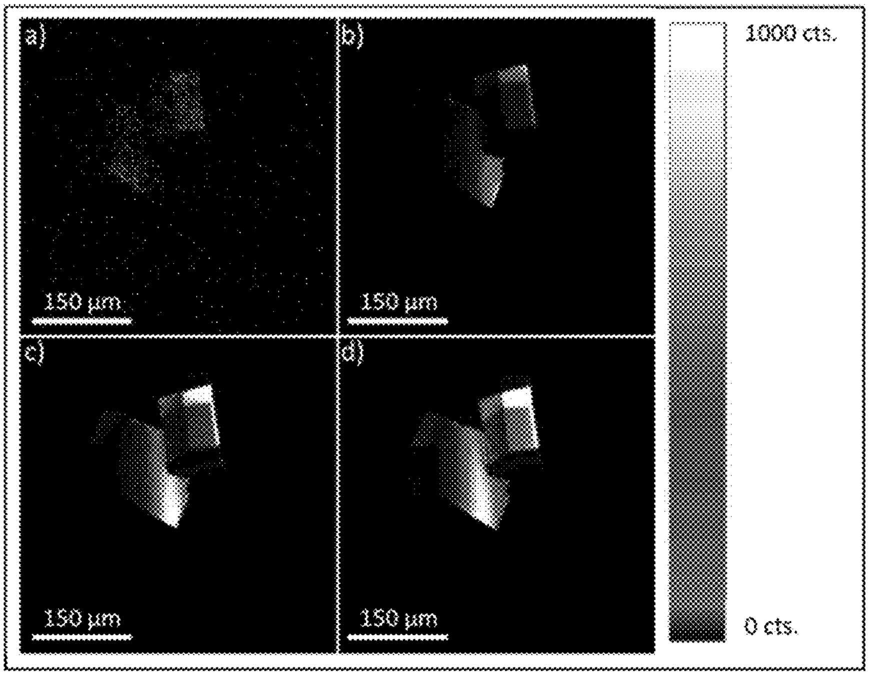
FIG. 1 contains images showing intercalation of a 500 μM solution of malachite green into lysozyme crystals. At time zero (a) there is no detectable SHG. The scale was adjusted to show low counts. Within minutes, a detectable signal was observed (b through d) with an overall SHG enhancement of about 700 after twelve minutes of dye intercalation.

The following describes the use of compounds capable of enhancing the SHG response of protein crystals in order to determine their 3-D structures. By incorporating (intercalation) such "SHG-active" compounds (sometimes referred to herein as "SHG-phores") into protein crystals, the compounds were determined to adopt a symmetry mirroring that of the underlying protein lattices to produce enhanced coherent SHG. Intercalation of the SHG-phores was further determined to decrease the number of false negatives for crystallization condition screening and increase the SNR for protein crystal detection.

The following discussion will describe certain investigations in which SHG activity of protein crystals was found to be greatly enhanced by intercalation of SHG-phores within the crystal lattice of proteins. The investigations were particularly designed to characterize the symmetry properties and enhancements of representative SHG-active dyes within selected protein crystal lattices. Lysozyme was selected as a protein for use in the investigations. Unlike the intercalation of fluorophores, the SHG-active dyes produced no significant background SHG from solvated dye or from dye intercalated into amorphous aggregates. The polarization-dependent SHG was consistent with the chromophores adopting the symmetry of the crystal lattice. In addition, the degree of enhancement for different symmetries of dyes was consistent with theoretical predictions based on the molecular nonlinear optical response. Kinetics studies indicated intercalation arose over a time frame of several minutes in lysozyme, with detectable enhancements within seconds. As such, results of the investigations indicated that intercalation of SHG-active dyes is a technique capable of providing a potential means to increase the overall diversity of protein crystals and crystal sizes amenable to characterization by SHG microscopy.

Crystallized lysozyme, polymorphs of glucose isomerase, and metallo deubiquitinating enzymes (DUBs) were utilized in the investigation. Crystallization of lysozyme was adapted from a previous method reported in Yaoi et al., Japanese Journal of Applied Physics 43, L1318 (2004), and briefly described here. Chicken egg-white lysozyme was purchased from Sigma-Aldrich (catalog No. L6876). A 25.0 mg $mL^{-1}$ lysozyme solution was prepared in 0.5 mL nanopure water and filtered through a 0.2 μm pore-size filter. Crystallization was achieved with a 7% (wt/wt) NaCl solution in acetate buffer prepared by mixing 3.75 mL of a 1:10 dilution of glacial acetic acid, 0.295 g sodium acetate, and 40 g NaCl and diluted to 500 mL with nanopure water. Tetragonal lysozyme crystals of $P_{4^32^12}$ were grown in 96-well crystallization plates (Corning). 100 μL of the NaCl/acetate buffer solution was added to the reservoir well. In the crystallization wells, 1 μL of NaCl/acetate buffer solution and 1 μL of lysozyme solution were added. The wells were sealed with tape and allowed to crystallize overnight.

The crystallization of $I_{222}$ and $P_{2^12^12}$ polymorphs of glucose isomerase crystals has been described in DeWalt et al., Analytical Chemistry 86, p 8448-8456 (2014), and therefore will only be briefly described here. A crystalline suspension of glucose isomerase (Hampton) was dialyzed against 10 mM HEPES, 1 mM $MgCl_2$ and 100 mM HEPES, 10 mM $MgCl_2$. To obtain the $P_{2^12^12}$ polymorph, the glucose isomerase solution was concentrated to 35 mg/mL and crystallized in 2.0 M ammonium sulfate (pH 7.4). The $I_{222}$ polymorph was obtained by concentrating to 26 mg/mL and crystallized in 0.7 M sodium citrate tribasic dehydrate (pH 7).

The investigation utilized crystals of the catalytic domain of the JAMM family of metallo deubiquitinating enzymes (DUBs) from *Schizosacharomyces pombe* ($Sst2^{cat}$). The domain was expressed in *E. coli* as a recombinant protein fused with a glutathione S-transferase (GST) tag at the N-terminus. The protein was purified using glutathione agarose beads and the GST tag was cleaved with PreScission protease (GE Biosciences). For crystallization, $Sst2^{cat}$ was concentrated to 20 mg/mL in a buffer consisting of 50 mM Tris-HCl, 50 mM NaCl, and 1 mM DTT (pH 7.6). Crystallization was performed by sitting drop vapour diffusion at room temperature. Crystals of $Sst2^{cat}$ were grown from the reservoir containing 0.2 M ammonium phosphate dibasic (pH 8.0) and 20% w/v polyethylene glycol (PEG) 3350. The crystals were obtained from a drop containing 1.5 μL protein solution and 1.5 μL reservoir solution.

SHG-active dye solutions of 500 μM malachite green oxalate salt (N,N,N',N'-Tetramethyl-4,4'-diaminotriphenylcarbenium oxalate; $C_{23}H_{25}N_2.C_2HO_4.0.5C_2H_2O_4$, hereinafter simply referred to as "malachite green") and trans-4-[4-dimethylamino)styryl]-1-methylpyridinium iodide (DMI) (both obtained from Sigma-Aldrich Co. LLC) were prepared in ethyl acetate. In addition and as discussed below, dye solutions of crystal violet ($C_{25}N_3H_{30}Cl$) were also utilized in the investigation. The dye solutions were introduced to the protein crystals within the wells of the crystallization plate by removing the tape used to seal the wells and then adding 1 μL of the dye solution to each well. The ethyl acetate was allowed time to evaporate before the wells were resealed and left for ten minutes to allow the dye to intercalate into the crystals.

SHG images were obtained using a custom-built beam-scanning SHG microscope. Beam scanning was performed with a resonant vibrating mirror (approximately 8 kHz, EOPC) along the fast-axis scan and a galvanometer (Cambridge) for slow-axis scanning. The incident beam was provided via 80 MHZ Ti:Sapphire pulsed laser (Spectra-Physics Mai Tai) of 100 fs pulse. The beam was focused on the sample with a 10× objective with a working distance of 1.6 cm (Nikon, N.A.=0.30). The incident wavelength was 1000 nm with 90 mW average power at the sample. Two thousand frames were collected and averaged with an average acquisition time of about two minutes. The SHG signal was collected with dichroic mirrors and narrow band-pass filters centered about 500 nm placed before the photomultiplier tube detectors (PMT). Two PMTs in transmission collected either the co-parallel or cross-polarized transmission. The incident beam was horizontally polarized and the vertical and horizontal components were collected separately. MatLab® code was written to control the scanning mirrors and communication with the data acquisition electronics. Image J was used to analyze and produce SHG images.

Crystals of Proteinase K were obtained by screening against the Crystal Screen HT (Hampton) protein crystal screening kit by sitting drop vapour diffusion in a 3-drop 96-well plate (Corning). The three crystallization wells contained 1 μL of 20 mg/mL Proteinase K (Sigma) in 25 mM HEPES (pH 7.0) with 1 μL of the respective crystal screen solution. The three wells contained dye concentrations of either 0 or 50 μM. The crystallization was performed for both malachite green and crystal violet dye solutions. The well plates were imaged using the automated SHG microscope SONICC (Formulatrix).

The results of malachite green intercalation into a lysozyme protein crystal are summarized in FIG. 1. Native tetragonal lysozyme crystals generated weak SHG signals exemplified in image 1*a* of FIG. 1, with significant signal averaging performed to visualize the protein crystals. The addition of an SHG-active dye was found to significantly increase the SHG activity and SNR of the image over a total intercalation time scale of twelve minutes (images b, c and d of FIG. 1). While the SHG enhancement was highly variable due to the dependence on crystal orientation and the challenge in accurately quantifying the weak initial responses, an average enhancement of about 4500 fold was achieved for the intercalation of malachite green into lysozyme protein crystals.

Figure 2:
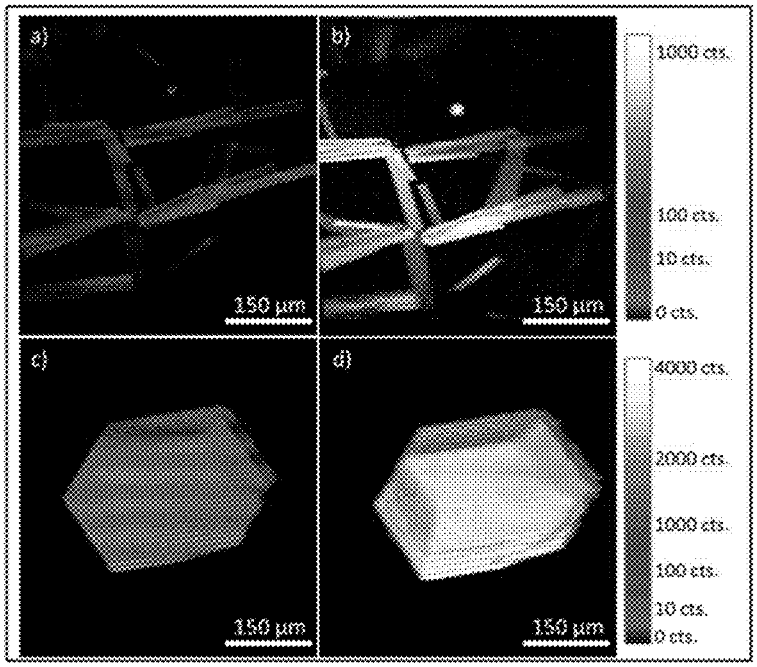
FIG. 2 contains images showing (a) undyed $P2_12_12$ glucose isomerase crystals, (b) intercalation of a 500 μM solution of malachite green into the $P_{2^12^12}$ crystals, (c) undyed $I_{222}$ glucose isomerase crystals, and (d) intercalation of a 500 μM solution of crystal violet into the $I_{222}$ crystals.

The universality of staining with an SHG-phore was examined by intercalating malachite green and crystal violet into the two aforementioned polymorphs of glucose isomerase. Results of the SHG enhancement for both the $I_{222}$ and $P_{2}{}^{1}{}_{2}{}^{1}{}_{2}$ polymorphs are shown in FIG. 2. Crystal violet was used to stain the $I_{222}$ polymorph (images a and b of FIG. 2), due to the use of citrate in the crystallization (vide infra). The enhancement of $I_{222}$ glucose isomerase was only on the order of a three-fold enhancement in SHG activity, which may have been due to differences in the degree of dye incorporation, the degree of dye ordering within the crystal, or the lowered native nonlinear optical activity of crystal violet relative to malachite green at the measurement wavelengths. The $P_{2}{}^{1}{}_{2}{}^{1}{}_{2}$ polymorph was stained with malachite green and an enhancement of about 1 order of magnitude was observed (images c and d of FIG. 2).

Figure 3:
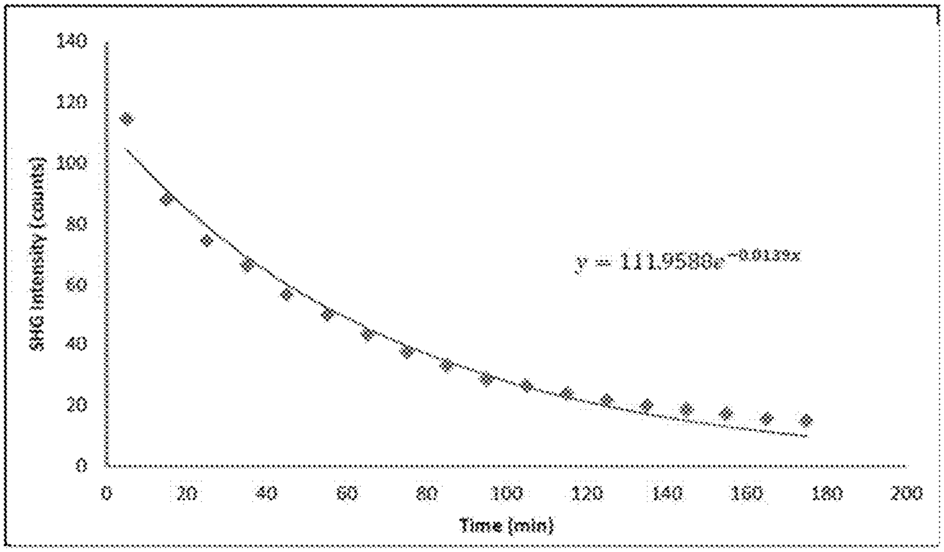
FIG. 3 is a graph indicating a 25-fold SHG enhancement initially observed for a DUB crystal dyed with malachite green, and evidences signal decay as a function of time.

Through experimentation with various different crystallization conditions, it was found that malachite green interacted with citrate and phosphate, resulting in a visible loss of the green color and likely reducing the resonance-enhanced SHG activity over time. For this reason, the structurally similar crystal violet was used for soaking crystals when citrate salts were used to induce crystallization. When added to the DUB crystals grown in ammonium phosphate and PEG, malachite green initially intercalated into the crystal and increased the protein's inherent SHG intensity by about 25-fold. However, within ten minutes this signal began to decrease following an exponential decay decreasing to about 10% of the original dyed signal before three hours (FIG. 3). This decrease in signal qualitatively tracked the visual loss of the green color within the wells. This effect was considered to be potentially attributable to the PEG successfully competing with the protein for the dye, or a chelating effect from the phosphate, similar to the effect seen with citrate.

Figure 6:
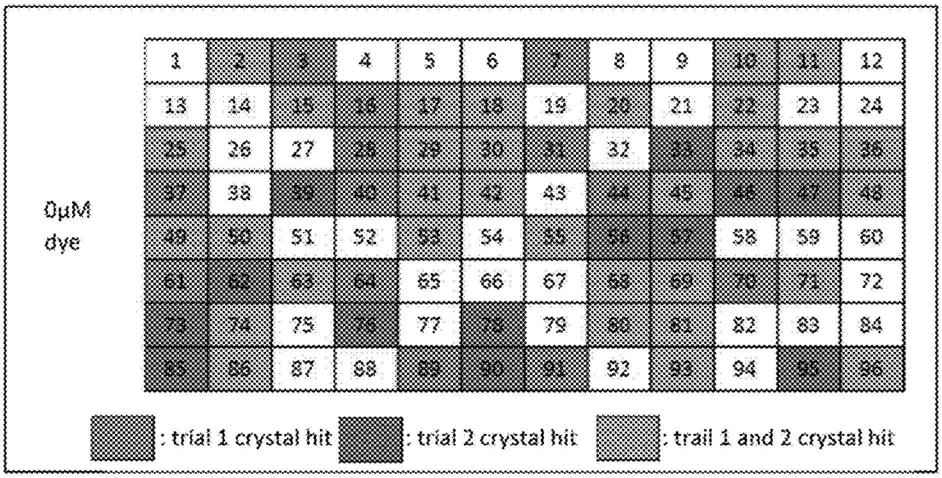
Figure 7:
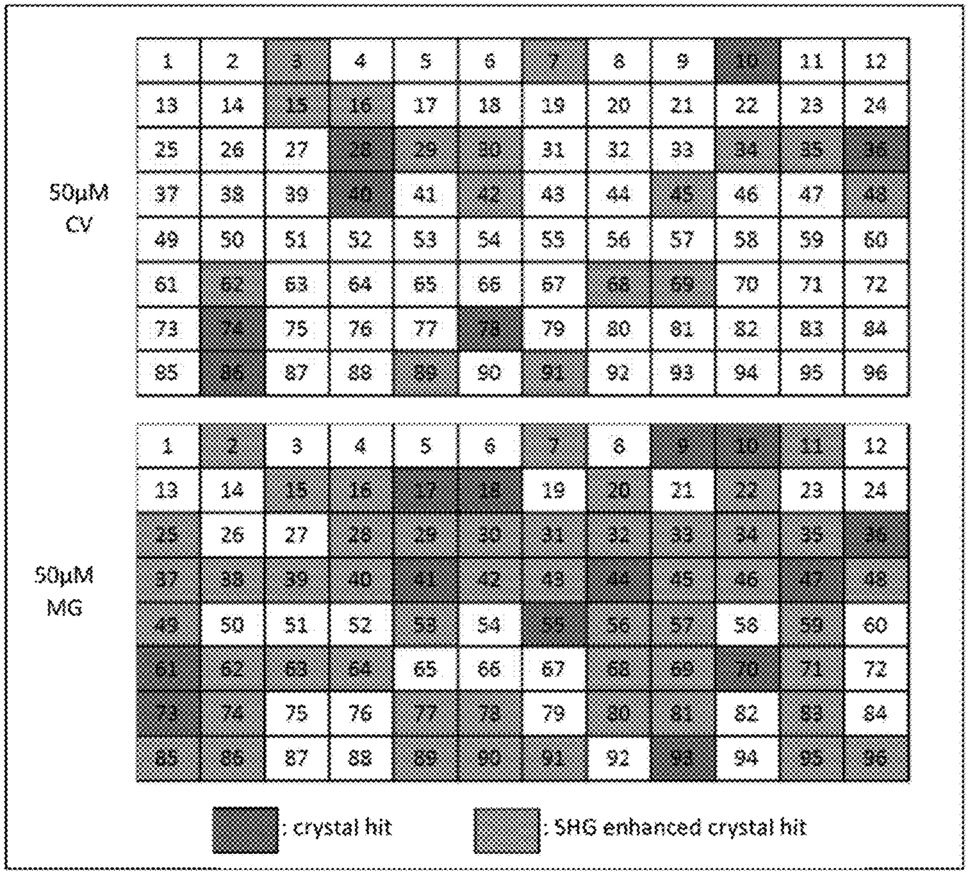

To further investigate the compatibility of the dyes with varying crystallization conditions, a crystal screen was performed for the crystallization of Proteinase K. The results of the screen for malachite green and crystal violet are summarized in Table 1 and FIGS. 6 and 7. A 106.9% hit rate for crystallization in the presence of malachite green compared to crystallization without dye was considered to be consistent with previous studies incorporating fluorescent dyes, indicating that the intercalation of the SHG-phores did not have a significant effect on the crystallization, size, or shape of the protein crystal. The elevated hit rate was well within the inherent variability for crystallization of Proteinase K without dye (found to be 28.9%). While it was noted that the hit rate for crystal violet (39.7%) did indicate that the dye significantly affected the crystallization of Proteinase K, both crystal violet and malachite green crystallization trials, respectively, resulted in sixteen and forty-nine different conditions exhibiting detectable SHG signal. In contrast, the undyed Proteinase K did not exhibit a detectable SHG signal, making high-throughput screening by SHG microscopy fruitless.

TABLE 1

| | No dye | CV | MG |
|---|---|---|---|
| Crystal Hits | 58* | 23 | 62 |
| Dye Hits/No Dye Hits (%) | — | 23/58 (39.7%) | 62/58 (106.9%) |
| # of Crystal Hits Exhibiting SHG (%) | 0 (0%) | 16 (69.6%) | 49 (79.0%) |

*28.9% variability between trials

Unlike fluorescence, coherent SHG is symmetry forbidden from isotropic or disordered media. Therefore, the mechanism of image contrast and signal generation was not inherent. It was conjectured that the presence of SHG arose from dye association at preferred locations within the protein (e.g., hydrophobic pockets), such that the dyes adopted the macromolecular symmetry of the lattice. Experiments were performed to test this hypothesis by measuring the polarization-dependent SHG and comparing the results to the expectations based on the lattice symmetry and the molecular symmetry.

The thermodynamically favored form of crystalline lysozyme in an aqueous environment is a tetragonal ($P_{4}{}^{3}{}_{2}{}^{1}{}_{2}$) structure. The corresponding $D_4$ point group of the crystal lattice allows for the following nonvanishing $\beta^{(2)}$ tensor elements in the crystal.

$$\beta_{xyz}=-\beta_{yxz}=\beta_{xzy}=-\beta_{yzx} \quad (1)$$

The local frame of the crystal is related to the laboratory frame through a rotation operation, expressed in terms of the Euler angles θ, ψ, and φ, describing the tilt, twist, and azimuthal rotation, respectively. In the laboratory frame for vertically polarized detection, the co-parallel detected SHG the $\chi^{(2)}$ tensor element is $\chi^{(2)}{}_{VVV}$ while the cross-polarized is $\chi^{(2)}{}_{VHH}$. For the four nonzero tensor elements in Eq. 1, the laboratory frame response of a tetragonal lysozyme crystal oriented by a set of angles (θ,ψ,φ) relative to the vertical axis is given by the following expression.

$$\chi_{VVV} \propto -(\beta_{xyz}+\beta_{xzy}+\beta_{yxz}+\beta_{yzx})\sin^2\theta\cos\theta\sin\psi\cos\psi$$

$$\chi_{VHH} \propto (\beta_{xyz}+\beta_{xzy})\sin^2\theta\cos\psi\cos\varphi(\cos\psi\sin\varphi+\cos\theta\sin\psi\cos\varphi) +(\beta_{yxz}+\beta_{zyx})\sin^2\theta\sin\psi\cos\varphi)(-\sin\psi\sin\varphi+\cos\theta\cos\psi\cos\varphi) \quad (2)$$

If the equalities between the $\beta^{(2)}$ tensor elements in the tetragonal lysozyme lattice in Eq. 1 are applied, the co-parallel and cross-polarized tensor elements simplify to the following relations.

$$\chi_{VVV}=0$$

$$\chi_{VHH}\propto\beta_{xyz}\sin^2\theta\sin\varphi\cos\varphi \quad (3)$$

Irrespective of the crystal orientation, the expression above demands that only cross polarized SHG can only be coherently produced by the tetragonal lysozyme lattice, consistent with experimental observations by others. All crystals of $D_4$ and $D_6$ symmetry share this same requirement. In contrast, the molecular tensor for malachite green has been found previously to be dominated by the $\beta_{zxx}$ tensor element for SHG measurements with a fundamental wavelength of about 800 nm, which can contribute to both coparallel and cross-polarized SHG depending on the molecular orientation. Experimentally, the SHG signal from native lysozyme crystals (without the SHG-phore) was only detectable for cross-polarized SHG measured in transmission, consistent with the expectations based on symmetry and previous similar measurements. Therefore, the observation of a strong preference for crossed polarized SHG from lysozyme crystals incorporating the SHG-phores would support a mechanism in which the dyes adopt the symmetry of the underlying crystal lattice.

Figure 4:
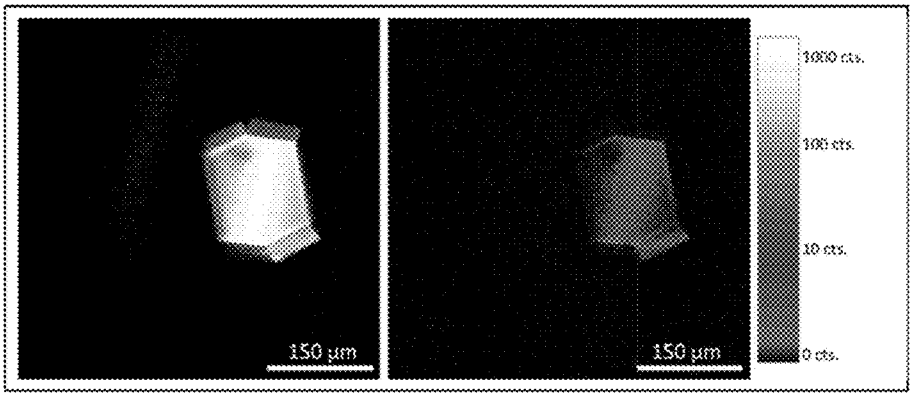
FIG. 4 shows (a) cross polarized and (b) coparallel SHG images of lysozyme soaked in malachite green acquired from the same crystal.

Polarization-dependent measurements of dye-incorporated lysozyme crystals are shown in FIG. 4. Consistent with the theoretical predictions for a templating interaction, the SHG intensity from the SHG-enhanced crystals was predominantly cross-polarized. This observation suggested that the SHG-phore adopts the symmetry of the lattice, consistent with preferred and oriented association with the proteins in the lattice.

In addition to the symmetry of the lattice, the symmetry of the SHG-phore is believed to play a significant role in the degree of anticipated enhancement. Previous theoretical work suggested that SHG-activity would generally be optimized for chiral crystals containing Λ-like chromophores, in which the low-lying transition moments is perpendicular to the charge-transfer axis. This molecular design principle led to the consideration of malachite green and crystal violet as potential candidates as crystal SHG-phores. In contrast, the fraction of the total hyperpolarizability surviving the symmetry operations of the lattice is substantially reduced in "rod-like" chromophores, in which the hyperpolarizability is dominated by interactions along a single internal axis within the chromophore. In this limit, the molecular tensor is dominated by the $\beta_{zzz}$ tensor element. Because all three indices are interchangeable within the molecular tensor, that same interchangeability must also hold in the macroscopic $\beta^{(2)}$ tensor of the crystal. In the case of tetragonal lysozyme, this interchangeability requires all the elements in Eq. 1 to also equal $\beta_{zxz}$, which is already zero from the symmetry operations of the lattice.

Figure 5:
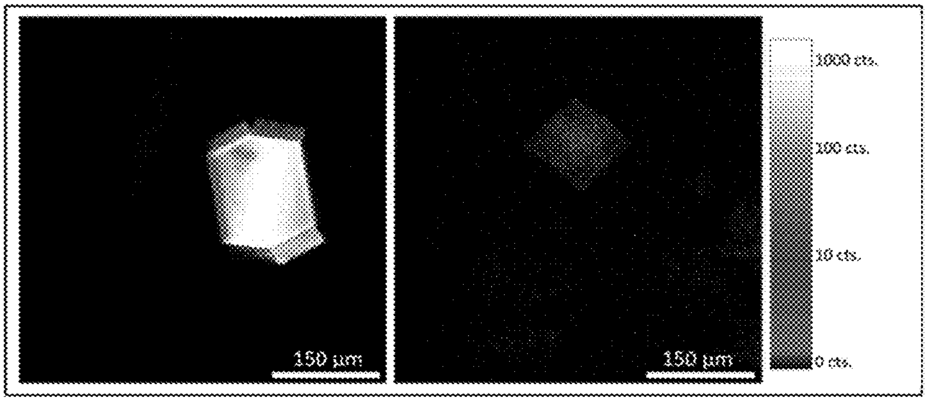
FIG. 5 evidences signal enhancement from Λ-like chromophores vs rod-like chromophores.

Experiments to test the prediction of stronger enhancements from Λ-like chromophores (e.g., malachite green and crystal violet) relative to rod-like chromophores were performed using the aforementioned DMI solution. In DMI, the long molecular axis of the chromophore dominates the nonlinear optical activity. As shown in FIG. 5, the enhancement from Λ-like malachite green was roughly 4500-fold, while that of rod-like DMI was only 30-fold. This value is an upper limit due to DMI also producing a two photon excited fluorescence background, which may have interfered with the detection of the SHG.

From the investigations discussed above, it was concluded that the use of certain SHG-active dyes were shown to enhance the SHG activity and increase the SNR for imaging protein crystals. Malachite green and crystal violet offered enhancements compared to DMI, with malachite green appearing to offer the strongest enhancements. However, a notable aspect of crystal violet was that it exhibited no significant interference from the presence of citrate salts, which were observed to reduce the resonance enhanced SHG activity of malachite green. Polarization-dependent measurements were consistent with the SHG-phores adopting the symmetry of the lattice, producing only cross-polarized SHG in studies of tetragonal lysozyme crystals. Enhancements ranging from about three-fold to greater than four thousand-fold were observed for three different proteins and multiple crystal polymorphs. The variability in the enhancement was concluded to likely arise from a combination of multiple effects, including but not limited to differences in the initial SHG-activity of the protein crystal, the degree of SHG-phore incorporation, the degree of ordering of the incorporated SHG-phores, and the inherent hyperpolarizability of the SHG-phore. By adopting the symmetry of the lattice, soaking of SHG-phores still provided the same selectivity for protein crystals afforded by SHG, with no coherent background produced from disordered proteins, including aggregates and proteins in solution, thereby reducing the number of false negatives for crystallization condition screening by SHG microscopy.

While the embodiments described above included intercalation into existing crystals, it is foreseeable and within the scope of the invention that compounds may be added to proteins prior to crystal formation to improve the SHG response. In particular, a dye may be associated nonspecifically with the protein (e.g., by partitioning to hydrophobic moieties) as discussed above, or associated to specific sites in the protein that have a high binding affinity prior to or following crystallization. As a nonlimiting example, a protein of interest may be engineered to include the tetracysteine (TC) motif Cys-Cys-Pro-Gly-Cys-Cys, and FlAsH-EDT2 or ReAsH-EDT2 labeling reagents may be bound to the recombinant protein to form a fluorescent complex that may enhance SHG imaging after crystallization of the labeled protein or upon intercalation of the dye into engineered protein crystals. Preferably, the labeled proteins maintain their original lattice structure upon crystallization.

While the invention has been described in terms of specific embodiments, it is apparent that other forms could be adopted by one skilled in the art. For example, SHG-active compounds other than those noted could be identified or developed, and processing parameters and materials other than those noted could be employed. Therefore, the scope of the invention is to be limited only by the following claims.

The invention claimed is:

1. A method of determining a three-dimensional structure of a protein crystal, the method comprising:

incorporating a compound into a protein crystal, the compound enhancing the activity of the protein crystal to second harmonic generation;

illuminating the protein crystal with a sufficiently intense light to cause second harmonic generation by the protein crystal; and detecting a second harmonic generation response produced by the protein crystal that is suitable for protein structure determination by diffraction analysis.

2. The method according to claim 1, wherein the compound is incorporated to adopt a symmetry mirroring that of the lattice of the protein crystal.

3. The method according to claim 1, wherein the compound is an Λ-like chromophore in which the low-lying transition moments of the compound is perpendicular to the charge-transfer axis of the compound.

4. The method according to claim 1, wherein the compound is a dye.

5. The method according to claim 1, wherein the compound is intercalated into the protein crystal after crystallization.

6. The method according to claim 1, wherein the compound is malachite green oxalate salt.

7. The method according to claim 1, wherein the compound is crystal violet.

8. The method according to claim 1, wherein the compound is added prior to crystallization.

9. The method according to claim 1, wherein the compound targets a tetracysteine sequence.

10. The method according to claim 1, wherein the second harmonic generation response of the protein crystal is not detectable by diffraction analysis in the absence of the compound incorporated therein.

11. The method according to claim 1, wherein the illuminating step is performed by SHG microscopy.

12. The method according to claim 1, further comprising: determining the protein structure of the protein crystal.

* * * * *